United States Patent
Patsey

[11] 4,010,635
[45] Mar. 8, 1977

[54] SONIC INTERFERENCE SUPPRESSOR

[75] Inventor: John A. Patsey, Penn Hills Township, Allegheny County, Pa.

[73] Assignee: United States Steel Corporation, Pittsburgh, Pa.

[22] Filed: Mar. 17, 1976

[21] Appl. No.: 667,764

[52] U.S. Cl. .................. 73/67.8 S; 73/71.5 US
[51] Int. Cl.² ............................... G01N 29/04
[58] Field of Search .............. 73/67.8 S, 71.5 US, 73/67.7, 67.8 R, 67.9

[56] References Cited
UNITED STATES PATENTS

| | | | |
|---|---|---|---|
| 3,028,753 | 4/1962 | Joy | 73/67.8 S |
| 3,602,036 | 8/1971 | Peterson | 73/67.8 S |
| 3,798,961 | 3/1974 | Flambard et al. | 73/71.5 US |
| 3,847,016 | 11/1974 | Ziedonis | 73/71.5 US |

Primary Examiner—Richard C. Queisser
Assistant Examiner—John P. Beauchamp
Attorney, Agent, or Firm—Rea C. Helm

[57] ABSTRACT

A sonic interference suppressor has a wiper of flexible material for wiping loose foreign material and excess water from a weld during ultrasonic inspection of the weld. A thin film of water between the contour conforming wiper and the weld passes unwanted ultrasonic energy into the wiper and on into foamed backing material.

5 Claims, 2 Drawing Figures

SONIC INTERFERENCE SUPPRESSOR

This invention relates to ultrasonic inspection of welds and more particularly to the elimination of unwanted ultrasonic energy, created by weld surface conditions, which interfere with the detection of weld flaws.

In some types of ultrasonic weld inspection, the condition of the weld surface has a substantial influence on the quality of the inspection. Surface irregularities or uncontrolled couplant water on the surface or foreign matter on the surface cause ultrasonic energy reflections which interfere with, and often can act in the same manner as, ultrasonic energy signals detecting flaws. This seriously affects the reliability of the weld inspection. Some improvement is possible by blowing a stream of air against the weld surface or in some methods by moving the inspection head, with its couplant water, away from the weld but neither of these techniques adequately reduce interference.

In accordance with my invention a flexible wiper is used to wipe foreign material and excess water off the surface of the weld during the inspection. The wiper moves on a thin film of water which allows unwanted ultrasonic energy to pass into the wiper material and its backup material instead of reflecting back into the weld.

It is therefore an object of my invention to provide an apparatus that wipes off foreign material and excess water from a weld during ultrasonic inspection.

Another object of my invention is to provide an apparatus that allows unwanted ultrasonic energy to pass out of the weld surface instead of reflect back into the weld.

Figure 1:
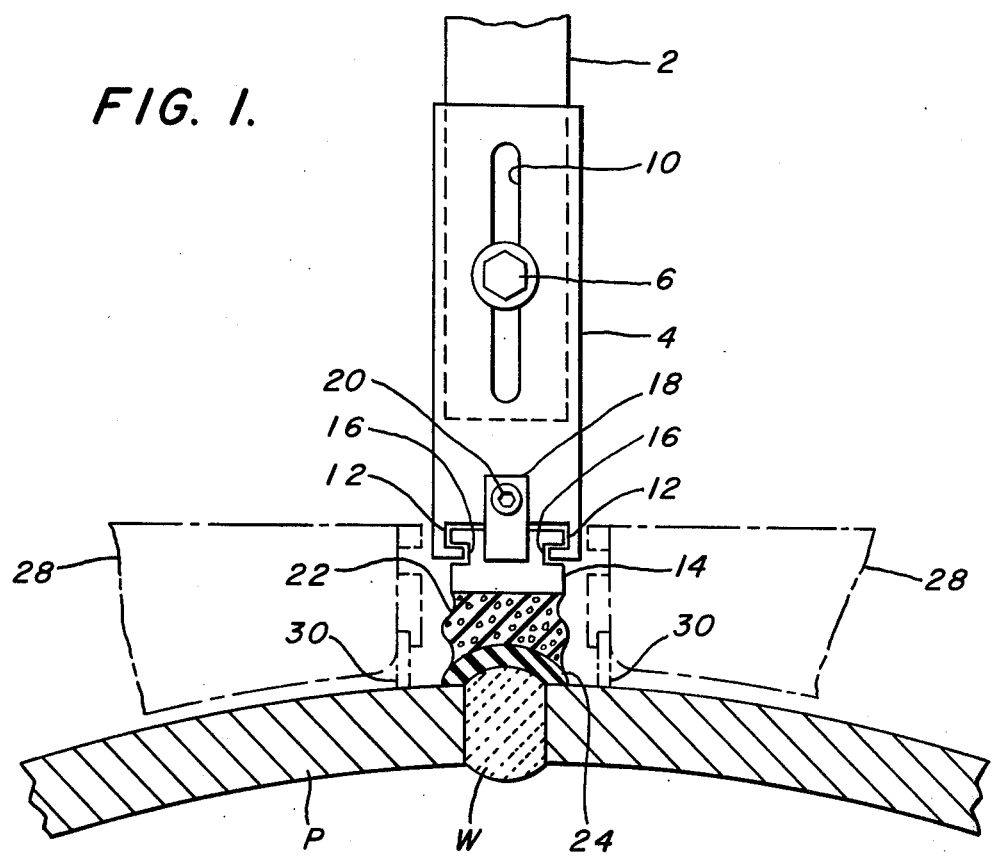
Figure 2:
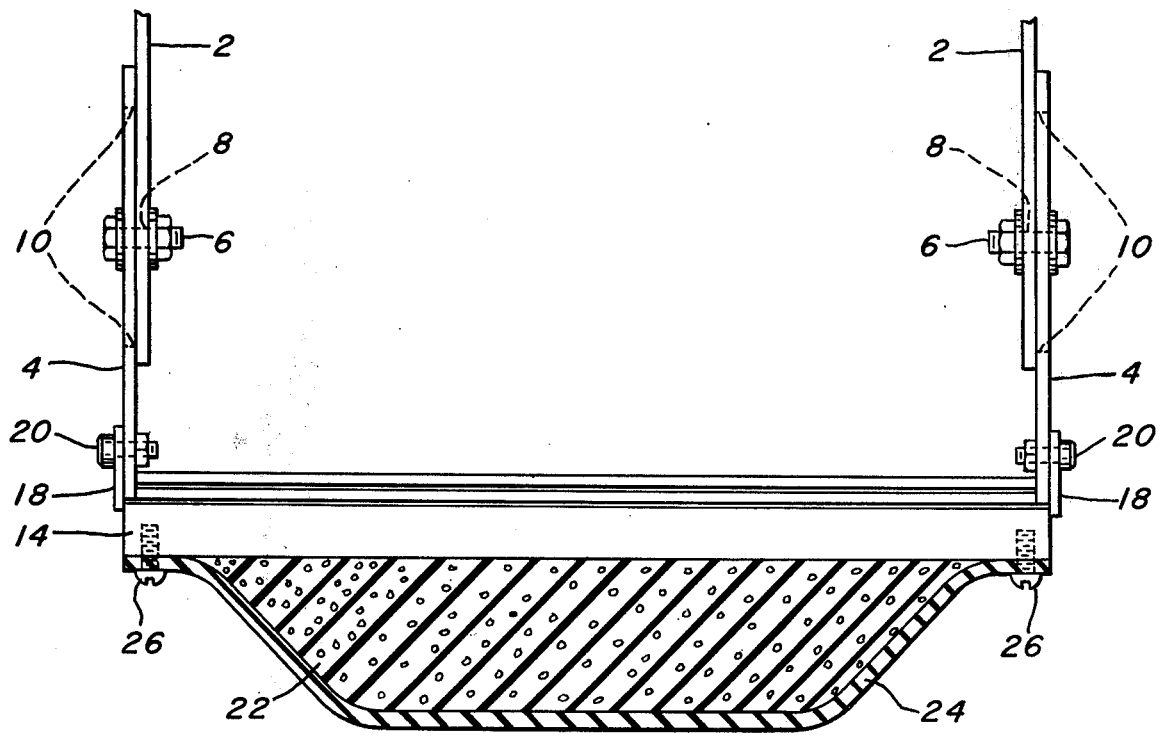

These and other objects will become more apparent after referring to the following specification and drawings in which:

FIG. 1 is an end view, partially in section, of the suppressor of my invention and FIG. 2 is a side view, partially in section, of the suppressor of my invention.

Referring now to the drawings, reference numeral 2 indicates portions of a supporting frame attached to an ultrasonic inspection apparatus (not shown) positioned over a weld W in a pipe P which is to be inspected by movement of the inspection apparatus along the weld. A U-shaped bracket 4 is attached for vertical adjustment to frame 2 by bolts 6 passing through holes 8 in frame 2 and slots 10 in the arms of bracket 4. Bracket 4 has a pair of longitudinal slots 12 adjacent the bottom face of bracket 4. A support member 14 has a pair of longitudinal slots 16 adjacent the top face of support member 14 mating with slots 12. A retainer 18 for support member 14 is attached to each end of bracket 4 by bolts 20. A resilient backing 22 of foamed polyurethane is attached to the bottom of support 14 by rubber cement. A wiper 24 of flexible polyurethane rubber passes around the ends and bottom of backing 22 and is attached to support member 14 by screws 26.

In operation, the inspection apparatus lowers frame 2 until wiper 24 contacts the weld, slightly compressing backing 22 so that the resiliency of backing 22 provides sufficient pressure for wiper 24 to conform to the contour of the weld. Wiper 24 then moves along the weld together with inspection heads 28. Blades 30 on inspection heads 28 are designed to prevent the escape of coupling water from the space between the bottom of the inspection heads and the surface of the pipe. However, as the blades move along the pipe surface, some water escapes towards the vicinity of the weld. The movement of wiper 24 along weld W wipes loose foreign material and excess water from the surface of the weld while maintaining a thin film of water between the weld surface and the wiper. Water may also be present from sources other than couplant water. The film acts as a sonic couplant allowing ultrasonic energy to pass from the weld into the material of wiper 24 and from there to be absorbed by backing material 22. This eliminates the interference or ultrasonic noise caused by rough surfaces and excessive couplant water on the weld. The ability of backing material 22 to absorb sound does not appear to be impaired by absorption of water.

While wiper 24 has been described as a flexible polyurethane rubber, other similar materials such as neoprene or rubber may also be used. Even though the thin film of water gives wiper 24 a surprisingly long life, the flexible polyurethane is preferred for its high resistance to abrasion. Backing 22 may be attached to support 14 in a manner other than described or not attached at all, being held in place only by wiper 24.

While my invention has been shown and described with reference to a particular embodiment thereof, it will be understood that changes and modifications may be made without departing from the scope of the following claims.

I claim:

1. An apparatus for the ultrasonic inspection of a weld joining the edges of material, wherein ultrasonic energy is directed through a liquid couplant and the surface of the material near the weld, the improvement comprising support means mounted for relative movement with respect to the weld in the direction of the longitudinal axis of the weld surface, a layer of flexible wiping material attached to the supporting means and in sliding contact with the weld surface during inspection and a backing member of resilient material located between the layer of wiping material and the support means.

2. Apparatus according to claim 1 in which the flexible wiping material is selected from the group consisting of rubber, neoprene and polyurethane rubber.

3. Apparatus according to claim 2 in which the flexible wiping material is polyurethane rubber.

4. Apparatus according to claim 3 in which the resilient material of the backing member is a foamed polyurethane.

5. Apparatus according to claim 4 which includes means connected to the support means for adjusting the spacing between the weld surface and a part of the support means next to the backing member.

* * * * *